(12) United States Patent
Ishibashi et al.

(10) Patent No.: US 6,338,910 B1
(45) Date of Patent: Jan. 15, 2002

(54) ORGANIC ELECTROLUMINESCENT DEVICE

(75) Inventors: Tadashi Ishibashi; Mari Ichimura; Shinichiro Tamura, all of Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 09/387,492

(22) Filed: Sep. 1, 1999

(30) Foreign Application Priority Data

Sep. 11, 1998 (JP) .......................................... 10-258462

(51) Int. Cl.$^7$ ............................................... H05B 33/14
(52) U.S. Cl. ...................... 428/690; 428/917; 428/704; 428/212; 313/504; 313/506; 257/40; 257/103
(58) Field of Search ................................. 428/917, 690, 428/704, 212; 313/504, 506; 257/40, 103

(56) References Cited

U.S. PATENT DOCUMENTS

| | | | |
|---|---|---|---|
| 4,197,120 A | | 4/1980 | Wright ......................... 430/32 |
| 5,126,214 A | * | 6/1992 | Tokailin et al. ............. 428/690 |
| 5,668,438 A | * | 9/1997 | Shi et al. ..................... 313/504 |

OTHER PUBLICATIONS

Patent Abstracts of Japan, vol. 014, No. 402 (P–1099), Aug. 30, 1990 & JP 02 154268 A (Konica Corp), Jun. 13, 1990, p. 591.
Patent Abstracts of Japan, vol. 018, No. 201, Apr. 8, 1994 & JP 06 001973 A. (Konica Corp), Jan. 11, 1994.
Patent Abstracts of Japan, vol. 1995, No. 10, Nov. 30, 1995 & JP 07 188649 A (Fuji Electric Co. Ltd), Jul. 25, 1995.
Tsutsui et al. "Molecular design of dyes and polymers for high–efficiency red electroluminescence", XP002126056.

* cited by examiner

Primary Examiner—Cynthia H. Kelly
Assistant Examiner—Ling Xu
(74) Attorney, Agent, or Firm—Sonnenschein, Nath & Rosenthal

(57) ABSTRACT

An organic electroluminescent device comprises an organic layer which has a luminescent region and which contains a distyryl compound represented by the following general formula (1).

Chemical formula 10 general formula (1):

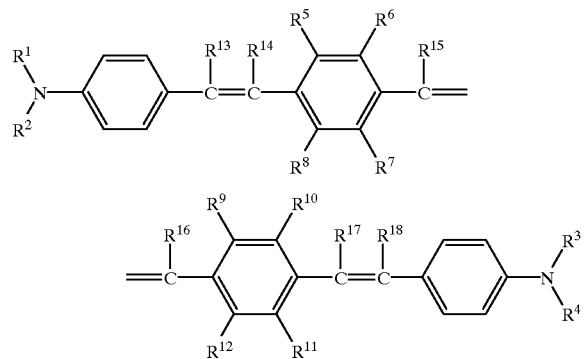

wherein $R^1$, $R^2$, $R^3$ and $R^4$ are, respectively, groups which may be the same or different and independently represent an aryl group of the following general formula (2), general formula (2):

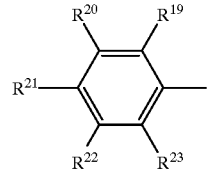

wherein $R^{19}$, $R^{20}$, $R^{21}$, $R^{22}$ and $R^{23}$ are, respectively, groups which may be the same or different and represent a hydrogen atom provided that at least one of them a saturated or unsaturated alkoxyl group, an alkyl group, an amino group or an alkylamino group, and $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are groups which may be the same or different provided that at least one of them represents a cyano group, a nitro group or a halogen atom.

8 Claims, 7 Drawing Sheets

EXAMPLE 1

EXAMPLE 2

EXAMPLE 3

EXAMPLE 5

EXAMPLE 1

EXAMPLE 2

ORGANIC ELECTROLUMINESCENT DEVICE

RELATED APPLICATION DATA

The present application claims priority to Japanese Application No. P10-258462 filed Sep. 11, 1998 which application is incorporated herein by reference to the extent permitted by law.

BACKGROUND OF THE INVENTION

This invention relates to an organic electroluminescent device (organic EL device) wherein an organic layer having a luminescent region is provided between an anode and a cathode.

Lightweight, highly efficient flat panel displays have been extensively studied and developed, for example, for picture display of computers and television sets.

Since cathode ray tubes (CRT) are high in luminance and exhibit good color reproducibility, they are most widely employed for display at present. Nevertheless, the problems are involved in that the tubes are bulky, heavy and high in power consumption.

For lightweight flat panel displays of high efficiency, there have been put on the market liquid crystal displays of the active matrix drive type. However, liquid crystal displays have the problems that their angle of field is narrow, they do not rely on spontaneous light and thus need great power consumption for back light when placed in a dark environment, and they do not have a sufficient response to high-speed video signals of high fineness which have been expected as being in use in future. Especially, a difficulty is involved in making a liquid crystal display with a large picture size, along with a problem on its high fabrication costs.

As a substitute therefor, a display of the type using a light-emitting diode may be possible, but such a display is also high in fabrication costs, coupled with another problem that it is difficult to form a matrix structure of light-emitting diodes on one substrate. Thus, when considered as a candidate for a low-cost display used in place of cathode ray tubes, this type of display has a great problem to solve before putting to practical use.

As a flat panel display which has the possibility of solving these problems, attention has been recently paid to organic electroluminescent devices (organic EL devices) using organic luminescent materials. More particularly, when using organic compounds as a luminescent material, it has been expected to realize a flat panel display, which makes use of spontaneous light, has a high response speed and has no dependence on an angle of field.

The organic electroluminescent device is so arranged that an organic thin film, which contains a luminescent material capable of emitting light through charge of an electric current, is formed between an optically transparent anode and a metallic cathode. In the research report published in Applied Physics Letters, Vol. 51, No. 12, pp. 913 to 915 (1987), C. W. Tang, S, A, VanSlyke, etc., set forth a device structure (an organic EL device having a single hetero structure), which has a double-layered structure including, as organic thin films, a thin film composed of a hole transport material and a thin film composed of an electron transport material. In the device, luminescence occurs by re-combination of holes and electrons charged from the respective electrodes into the organic films.

In this device structure, either of the hole transport material or the electron transport material serves also as a luminescent material. Luminescence takes place in a wavelength band corresponding to the energy gap between the ground state and the excited state of the luminescent material. When using such a double-layered structure, a drive voltage can be remarkably reduced, along with an improved luminescent efficiency.

Thereafter, there has been developed a three-layered structure (organic EL device having a double hetero structure) of a hole transport material, a luminescent material and an electron transport material as set out in the research report of C. Adachi, S. Tokita, T. Tsutsui and S. Saito, published in Japanese Journal of Applied Physics, Vol. 27, No. 2, pp. L269 to L271 (1988). Moreover, a device structure comprising a luminescent material present in an electron transport material has been developed as set out in the research report of C. W. Tang, S. A. VanSlyke and C. H. Chen published in Journal of Applied Physics, Vol. 65, No. 9, pp. 3610 to 3616 (1989). Through these researches, evidence has been given to the possibility of luminescence of high luminance at low voltage, thus leading to recent, very extensive studies and developments.

Organic compounds used as a luminescent material are considered to be advantageous in that because of their diversity in kind, a luminescent color can be arbitrarily changed theoretically by changing their molecular structure. Accordingly, it may be easier on comparison with thin film EL devices using inorganic materials to provide, via proper molecular design, three colors of R (red), G (green) and B (blue) having good color purities necessary for full color displays.

However, organic electroluminescent devices still have problems to solve. More particularly, a difficult is involved in the development of a stable red luminescent device with high luminance. In an instance of red luminescence attained by doping DCM[4-dicyanomethylene-6-(p-dimethylaminostyryl)-2-methyl-4H-pyran] in tris(8-quinolinol)aluminium (hereinafter abbreviated as $Alq_3$) for use as a currently reported electron transport material, this material is not satisfactory as a display material with respect to both maximum luminance and reliability.

BSB-BCN, which was reported by T. Tsutsui and D. U. Kim in the meeting of Inorganic and Organic Electroluminescence (in Berlin, 1996), is able to realize a luminance as high as 1000 $cd/m^2$ or over, but is not always perfect with respect to the chromaticity for use as a red color for full color display.

It is now demanded how to realize a red luminescent device which is high in luminance, stable and high in color purity.

In Japanese Patent Laid-open No. Hei 7-188649 (Japanese Patent Application No. Hei 6-148798), it has been proposed to use a specific type of distyryl compound as an organic electroluminescent material. However, the intended luminescent color is blue, not for red.

SUMMARY OF THE INVENTION

An object of the invention is to provide an organic electroluminescent device, which ensures high luminance and stable red luminescence.

Intensive studies have been made in order to solve the above-stated problems of the prior art, and as a result, it has been found that when using a specific type of distyryl compound as a luminescent material, there can be provided a highly reliable red luminescent device which is very useful for realizing a stable full color display of high luminance.

More particularly, there is provided, according to the invention, an organic electroluminescent device of the type which comprises an organic layer which has a luminescent region and is provided between an anode and a cathode and which contains, as an essential component, an organic material capable of generating luminescence by application of an electric current, wherein the organic layer contains, as an organic luminescent material, a distyryl compound represented by the following general formula (1) or (3)

Chemical formula 3 general formula (1):

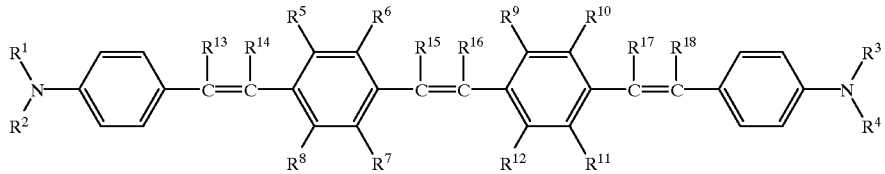

wherein $R^1, R^2, R^3$ and $R^4$ are, respectively, groups which may be the same or different and independently represent an aryl group of the following general formula (2), general formula (2):

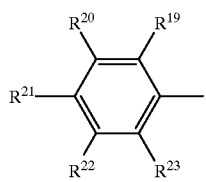

wherein $R^{19}$, $R^{20}$, $R^{21}$, $R^{22}$ and $R^{23}$ are, respectively, groups which may be the same or different and represent a hydrogen atom provided that at least one of them a saturated or unsaturated alkoxyl group, an alkyl group which is preferably a methyl group or a tertiary butyl group, an amino group or an alkylamino group, and $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are groups which may be the same or different provided that at least one of them represents a cyano group, a nitro group or a halogen atom such as F, Cl, Br or I.

general formula (3):

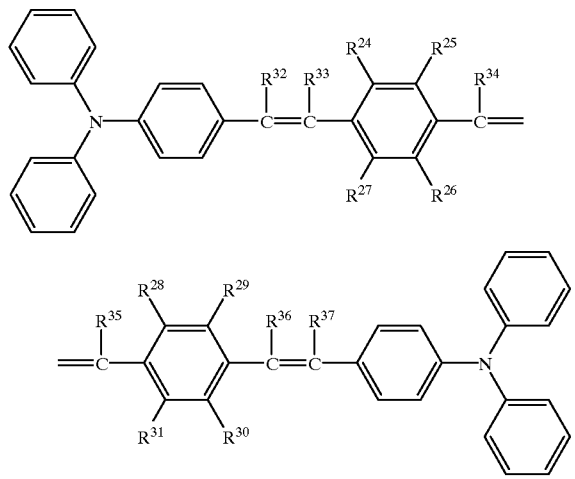

wherein $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$ and $R^{37}$ are groups which may be the same or different (and represent a hydrogen atom) provided that at least one of them represents a cyano group, a nitro group or a halogen atom such as F, Cl, Br or I.

The use, as a luminescent material, of a distyryl compound of the above general formula (1) and/or (3) enables one not only to obtain stable red luminescence of high luminance, but also to provide a device which has electrically, thermally or chemically good stability.

DESCRIPTION OF THE PREFERRED EMBODIMENTS

Figure 1:
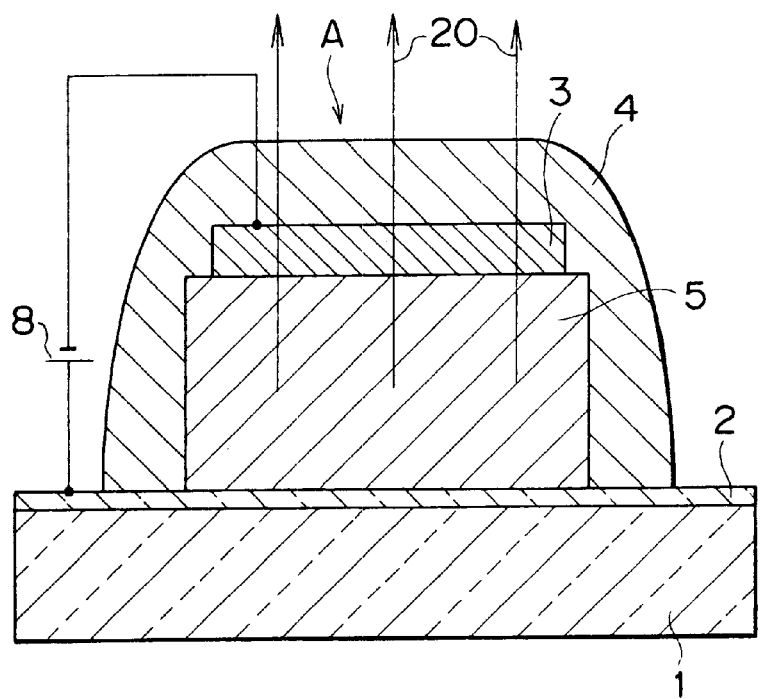
FIG. 1 is a schematic sectional view of an essential part of an organic electroluminescent device according to the invention.

The distyryl compounds used in the organic electroluminescent device of the invention are now described.

The distyryl compound represented by the general formula (1) and used as a luminescent material in the organic electroluminescent device of the invention may be one having at least one of molecular structures, for example, of the following structural formulas (4)-1, (4)-2, (4)-3, (4)-4, (4)-5, (4)-6 and (4)-7. All of the compounds consist of bis(aminostyryl) stilbene compounds having alkoxy (or alkyl) phenyl or unsubstituted phenyl group or groups.

Chemical Formula 4
Structural formula (4)-1:
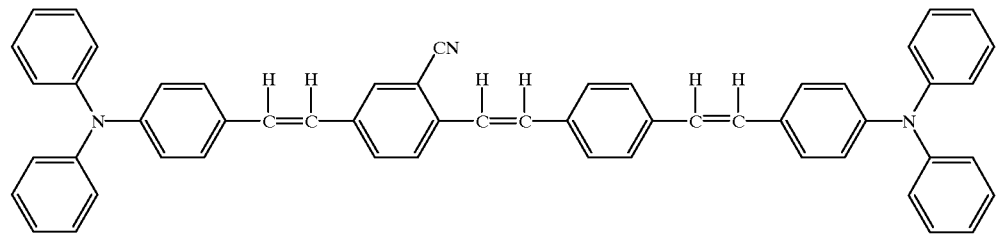
Structural formula (4)-2:
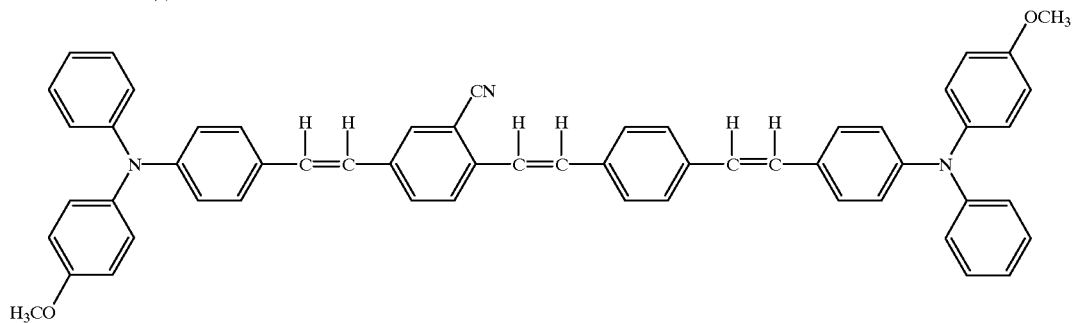
Structural formula (4)-3:
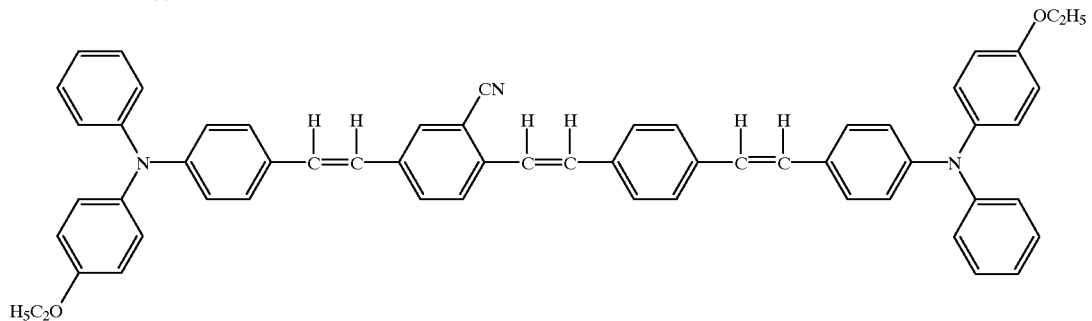
Structural formula (4)-4:
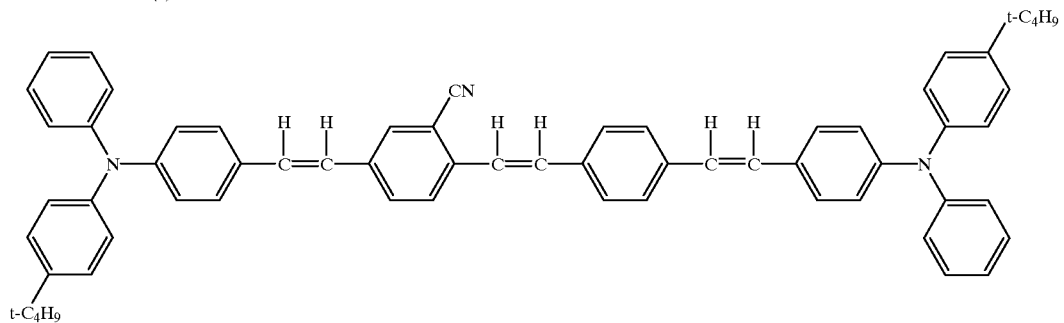

Structural formula (4)-5:

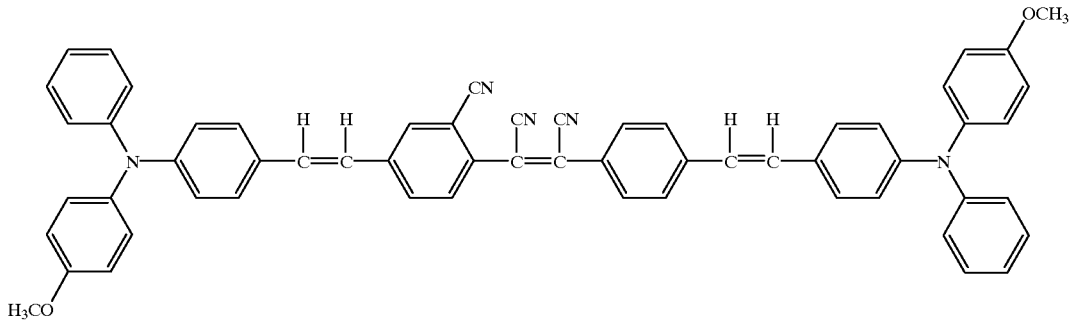

Structural formula (4)-6:

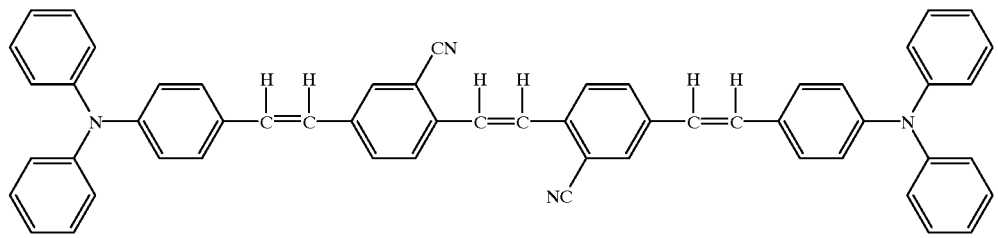

Structural formula (4)-7:

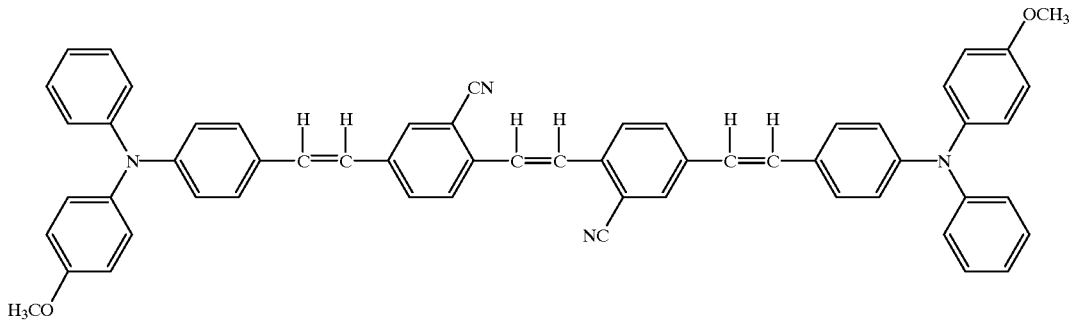

FIGS. 1 to 4, respectively, show examples of organic electroluminescent devices according to the invention, in which like reference numerals indicate like parts or members, respectively.

Figure 2:
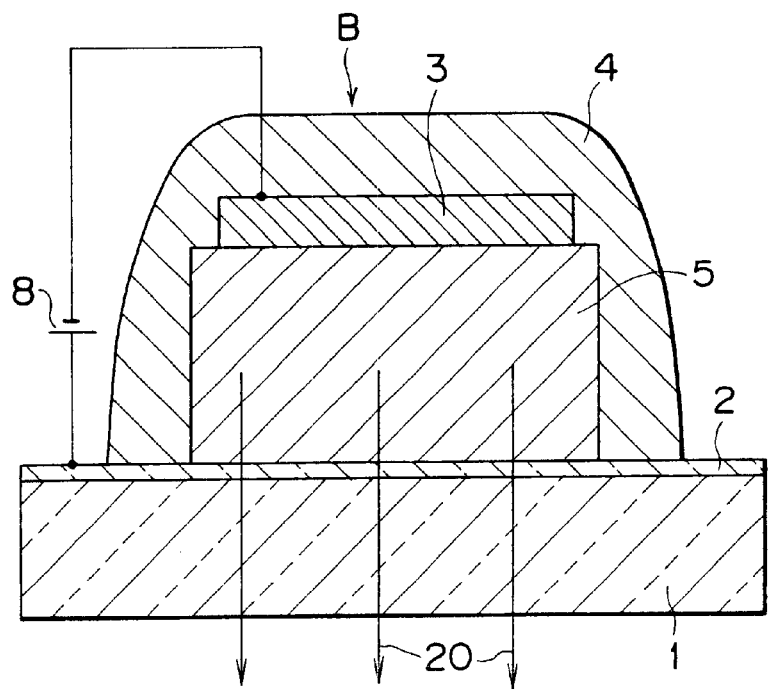
FIG. 2 is a schematic sectional view of an essential part of another type of organic electroluminescent device according to the invention.

FIG. 1 shows organic electroluminescent device A of a transmission type in which luminescent light 20 passes through a cathode 3, and the light 20 can also be observed from a side of a protective layer 4. FIG. 2 shows organic electroluminescent device B of a reflection type wherein light reflected at a cathode 3 can also be obtained as luminescent light 20.

In the figures, reference numeral 1 indicates a substrate for forming an organic electroluminescent device, which may be made of glass, plastics and other appropriate materials. Where the organic electroluminescent device is used in combination with other types of display devices, the substrate 1 may be commonly used. Reference numeral 2 indicates a transparent electrode (anode), for which ITO (indium tin oxide), $SnO_2$ or the like may be used.

Reference numeral 5 indicates an organic luminescent layer, which contains the above-mentioned distyryl compound as a luminescent material. For a layer arrangement for obtaining the luminescent light 20, the luminescent layer 5 may have hitherto known various types of layer arrangements. As is described hereinafter, if a material for either a hole transport layer or an electron transport layer has luminescent properties, for example, a built-up structure of these thin films may be used. Further, in order to increase charge transportability within a range satisfying the purposes of the invention, either or both of a hole transport layer and an electron transport layer have a built-up structure of thin films made of plural types of materials, or a thin film composed of a mixture of plural types of materials may be used without limitation. In addition, in order to improve luminescent properties, at least one fluorescent material may be used to provide a structure wherein a thin film of the fluorescent material is sandwiched between a hole transport layer and an electron transport layer. Alternatively, another type of structure may be used wherein at least one fluorescent material is present in a hole transport layer or an electron transport layer, or in both of them. In these cases, in order to improve a luminescent efficiency, a thin film for controlling the transport of holes or electrons may be incorporated in a layer arrangement.

The distyryl compounds represented by the structural formulas (4)-1 to (4)-7 have both electron transportability and electron transportability, and can be used as a luminescent layer serving also as an electron transport layer, or as a luminescent layer serving as a hole transport layer in the device arrangement. Moreover, it is possible to provide an arrangement wherein a distyryl compound is formed as a luminescent layer sandwiched between an electron transport layer and a hole transport layer.

It will be noted that in FIGS. 1 and 2, reference numeral 3 indicates a cathode, and an electrode material therefor may be made of an alloy of an active metal, such as Li, Mg, Ca or the like, and a metal, such as Ag, Al, In or the like. Alternatively, a built-up structure of thin films of these metals may also be used. In the transmission-type organic electroluminescent device, an optical transmission required for an intended application can be obtained by controlling a cathode thickness. In the figures, reference numeral 4 indicates a sealing/protecting layer, and when an organic electroluminescent device is wholly covered therewith, its effect increases. Appropriate materials may be used for this provided that air tightness is ensured. Reference numeral 8 indicates a drive power supply for current charge.

In the organic electroluminescent device of the invention, the organic layer may have an organic built-up structure (single hetero structure) wherein a hole transport layer and an electron transport layer are built up and wherein the above-mentioned distyryl compound is used as a material for forming the hole transport layer or electron transport layer. Alternatively, the organic layer may have an organic built-up structure (double hetero structure) wherein a hole transport layer, a luminescent layer and an electron transport layer are successively built up, and the luminescent layer is formed of the above-mentioned distyryl compound.

An example of an organic electroluminescent device having such an organic built-up structure is shown. More particularly, FIG. 3 shows organic electroluminescent device C having a single hetero structure which consists of a built-up structure comprising, on an optically transparent substrate 1, an optically transparent anode 2, an organic layer 5*a* consisting of a hole transport layer 6 and an electron transport layer 7, and a cathode 3 superposed successively in this order, and the built-up layer structure is sealed with the protective layer 4.

Figure 3:
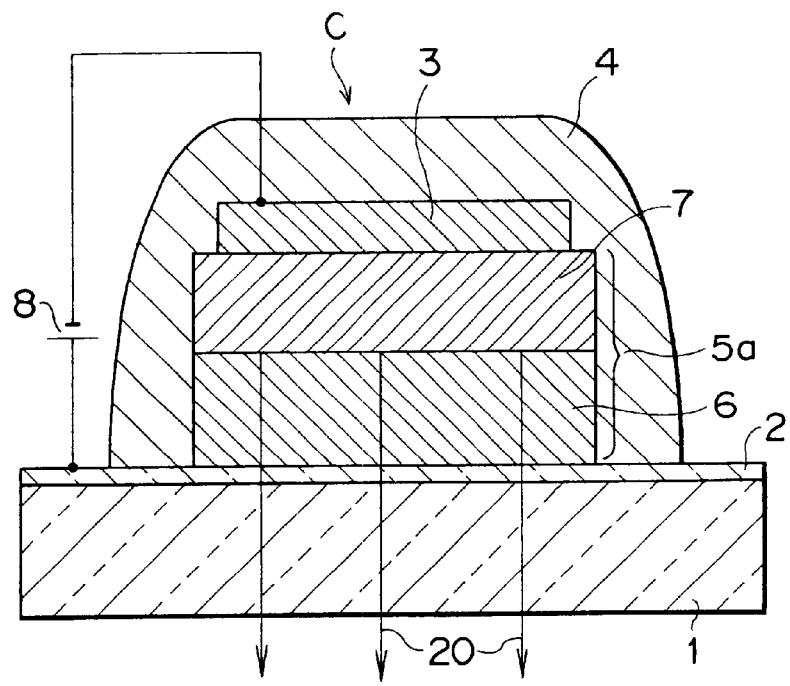
FIG. 3 is schematic sectional view of an essential part of other type of organic electroluminescent device according to the invention.

With such a layer arrangement as shown in FIG. 3 wherein a luminescent layer is omitted, the light 20 with a given wavelength is emitted from the interface between the hole transport layer 6 and the electron transport layer 7. This light is observed from the side of the substrate 1.

Figure 4:
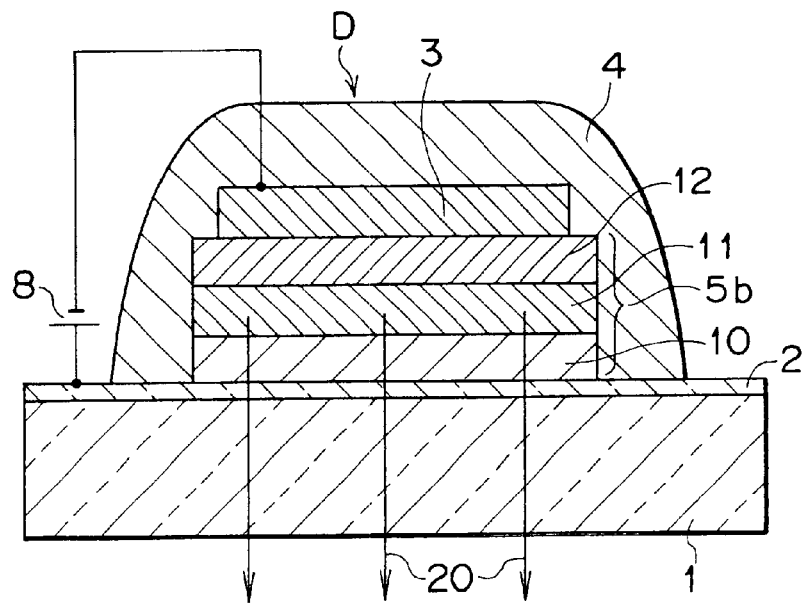
FIG. 4 is a schematic sectional view of an essential part of still other type of organic electroluminescent device according to the invention.

FIG. 4 shows organic electroluminescent device D having a double hetero structure which consists of a built-up structure comprising, on an optically transparent substrate 1, an optically transparent anode 2, an organic layer 5*b* consisting of a hole transport layer 10, a luminescent layer 11 and an electron transport layer 12, and a cathode 3 superposed successively in this order. The built-up structure is sealed with a protective layer 4.

In the organic electroluminescent device D shown in FIG. 4, when a DC voltage is applied between the anode 2 and the cathode 3, the holes charged or injected from the anode 2 arrives at the luminescent layer 11 via the hole transport layer 10, and the electrons injected from the anode 3 also arrives at the luminescent layer 11 via the electron transport layer 12. Eventually, the electrons/the holes are re-combined in the luminescent layer 11 to generate singlet excitons, thereby causing light with a given wavelength to be generated from the singlet excitons.

In the above-stated organic electroluminescent devices C and D, optically transparent materials such as, for example, glass, plastics and the like may be appropriately used as the substrate 1. Where the devices are used in combination with other types of display devices, or where the built-up structures shown in FIGS. 3 and 4 are arranged in the form of a matrix, the substrate may be commonly used. Both of the devices C and D may have a structure of either a transmission type or a reflection type.

The anode 2 consists of a transparent electrode, for which ITO (indium tin oxide), $SnO_2$ or the like may be used. In order to improve a charge injection efficiency, a thin film made of an organic material or an organometallic compound may be provided between the anode 2 and the hole transport layer 6 (or the hole transport layer 10). It will be noted that where the protective layer 4 is formed of a conductive material such as a metal, an insulating film may be provided at the sides of the anode 2.

The organic layer 5*a* of the organic electroluminescent device C consists of a built-up organic layer of the hole transport layer 6 and the electron transport layer 7. The afore-indicated distyryl compound may be contained in either or both of these layers to provide a luminescent hole transport layer 6 or electron transport layer 7. The organic layer 5*b* of the organic electroluminescent device D consists of a built-up organic layer of the hole transport layer 10, the luminescent layer 11 containing such a distyryl compound as set out before, and the electron transport layer 12. The layer 5*b* may take other various types of built-up structures. For instance, either or both of the hole transport layer and the electron transport layer may have luminescent properties.

Especially, it is preferred that the hole transport layer 6 or electron transport layer 7, and the luminescent layer 11, respectively, consist of a layer made of a distyryl compound used in the present invention. These layers may be formed of the afore-mentioned distyryl compound alone, or may be formed through co-deposition of the afore-mentioned distyryl compound and other type of hole or electron transport material (e.g. an aromatic amine, a pyrazoline or the like). Moreover, in order to improve the hole transportability in the hole transport layer, a hole transport layer, which consists of a plurality of hole transport materials being built up, may be formed.

In the organic electroluminescent device C, the luminescent layer may be the electron transport luminescent layer 7. In this case, light may be emitted from the hole transport layer 6 or its interface depending on the voltage applied to from a power supply 8. Likewise, in the organic electroluminescent device D, the luminescent layer may be, aside from the layer 11, the electron transport layer 12 or the hole transport layer 10. For improving the luminescent performance, it is preferred to provide a structure wherein the luminescent layer 11 containing at least one fluorescent material is sandwiched between the hole transport layer and the electron transport layer. Alternatively, a fluorescent material may be contained in the hole transport layer or the electron transport layer, or in both layers. In this connection, in order to improve a luminescent efficiency, a thin film (such as a hole blocking layer or an exciton-generating layer) for controlling the transport of holes or electrons may be provided in the layer arrangement.

The materials used as the cathode 3 may be alloys of active metals such as Li, Mg, Ca and the like and metals such as Ag, Al, In and the like. Alternatively, a built-up structure of the layers of these metals may also be used. Proper selection in cathode thickness and in type of alloy or metal enables one to fabricate an organic electroluminescent device adapted for its application.

The protective layer 4 acts as a sealing film, and is arranged to wholly cover an organic electroluminescent device therewith, thereby ensuring improved charge injection efficiency and luminescent efficiency. It should be noted that if air tightness is ensured, a material including a single metal such as aluminium, gold, chromium or the like or an alloy thereof may be appropriately selected for this purpose.

The electric current applied to the respective organic electroluminescent devices set out hereinbefore is usually direct current, but pulse current or AC current may also be used. The values of current and voltage are not critical provided that they are within ranges not breaking the devices down. Nevertheless, taking into account the power consumption and life of the organic electroluminescent devices, it is preferred to cause luminescence efficiently by use of an electric energy which is as small as possible.

Figure 5:
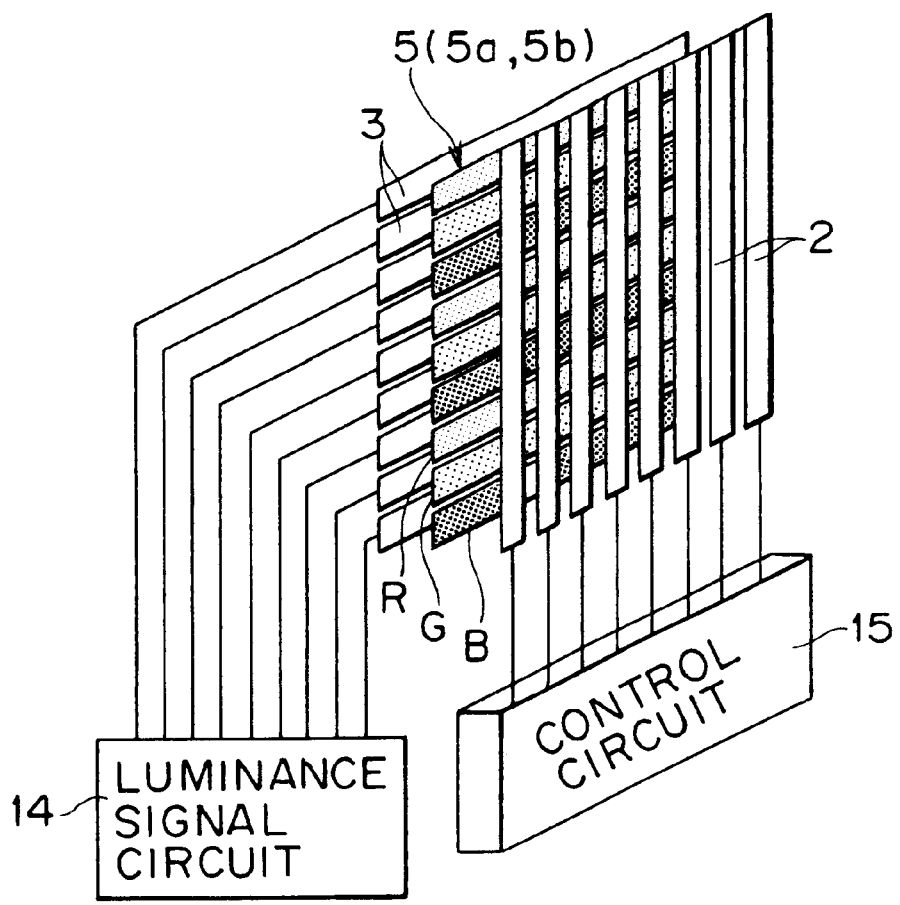
FIG. 5 is a view showing an arrangement of a full color flat display using an organic electroluminescent device according to the invention.

Next, FIG. 5 shows an arrangement of a flat display, which makes use of an organic electroluminescent device of the invention. As shown in the figure, with the case, for example, of a full color display, organic layers 5 (5a, 5b) capable of generating luminescent three primary colors of red (R), green (G) and blue (B) are arranged between cathodes 3 and anodes 2. The cathodes 3 and the anodes 2 may be provided in the form of a stripe in which they are mutually intersected, and are properly selected by means of a luminance signal circuit 14 and a shift register built-in control circuit 15 and applied with a signal voltage thereto. As a result, an organic layer at a position (picture element) where the selected cathode 3 and anode 2 are intersected emits light.

More particularly, FIG. 5 shows, for example, a 8×3 RGB simple matrix wherein a built-up body 5 consisting of a hole transport layer and at least one of a luminescent layer and an electron transport layer is provided between the cathodes 3 and the anodes 2 (see FIG. 3 or 4). The cathodes and anodes are patternized in the form of a stripe and are mutually intersected in a matrix, to which signal voltages are applied in time series from the shift register built-in control circuits 15 and 14, thereby causing electroluminescence or light emission at the intersected position. The EL device having such an arrangement may be used not only as a display for letters/symbols, but also as an image reproducing apparatus. Moreover, the striped patterns of the anodes 3 and the cathodes 2 may be arranged for each of red (R), green (G) and blue (B) colors, thus making it possible to fabricate a solid-state flat panel display of the multicolor or full color type.

The invention is more particularly described by way of examples, which should not be construed as limiting the invention thereto.

EXAMPLE 1

This example illustrates fabrication of an organic electroluminescent device having a single hetero structure using, as a hole transport luminescent material, a compound of the following structural formula (4)-1 selected among distyryl compounds of the general formula (1), wherein $R^1$, $R^2$, $R^3$ and $R^4$, respectively, represent a phenyl group and $R^6$ represents a cyano group A 30 mm×30 mm glass substrate, which had been formed with a 100 nm thick anode made of ITO on one surface thereof, was set in a vacuum deposition apparatus. A metallic mask having a plurality of 2.0 mm×2.0 mm unit openings was placed, as a deposition mask, closely to the substrate. The compound of the above structural formula (4)-1 was subjected to a vacuum deposition method at a vacuum of $10^{-4}$ Pa or below to form, for example, a 50 nm thick hole transport layer (serving also as a luminescent layer). The deposition rate was at 0.1 nm/second.

Further, $Alq_3$ (tris(8-quinolinol)aluminium) of the following structural formula was provided as an electron transport material and was deposited in contact with the hole transport layer. The electron transport layer made of $Alq_3$ was set at a thickness, for example, of 50 nm, and the deposition rate was at 0.2 nm/second.

Chemical formula 6

$Alq_3$:

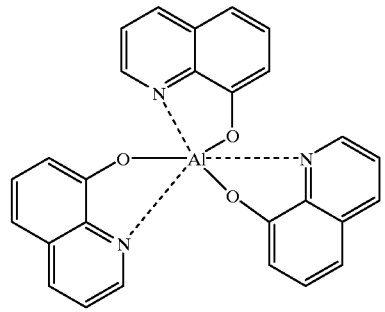

A built-up film of Mg and Ag provided as a cathode material was used. To this end, Mg and Ag were, respectively, deposited at a deposition rate of 1 nm/second to form, for example, a 50 nm thick Mg film and a 150 nm thick Ag film. In this way, an organic electroluminescent device as shown in FIG. 3 was fabricated in Example 1.

Figure 6:
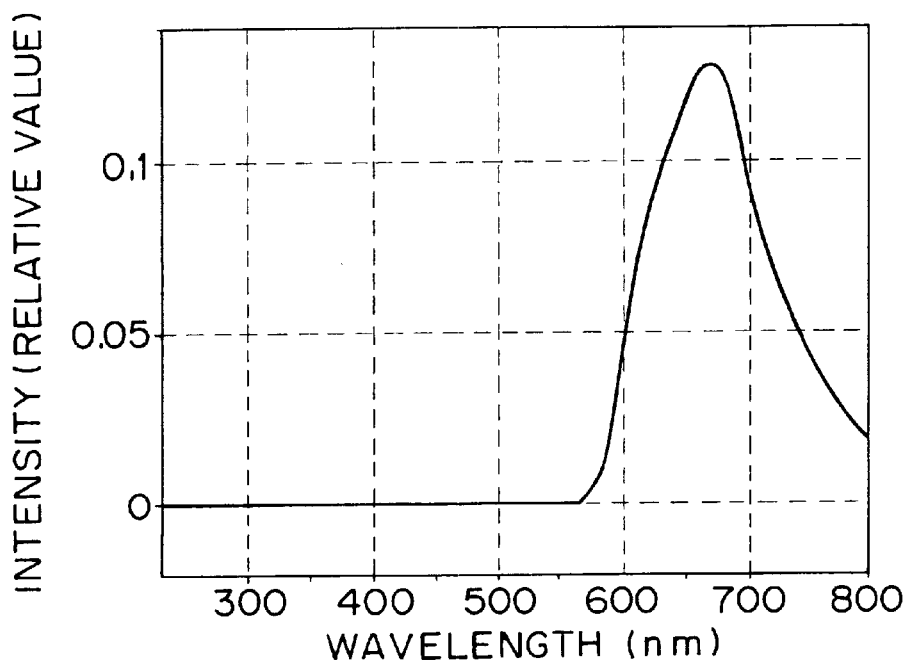
FIG. 6 is an emission spectrogram of an organic electroluminescent device of Example 1 of the invention.
Figure 10:
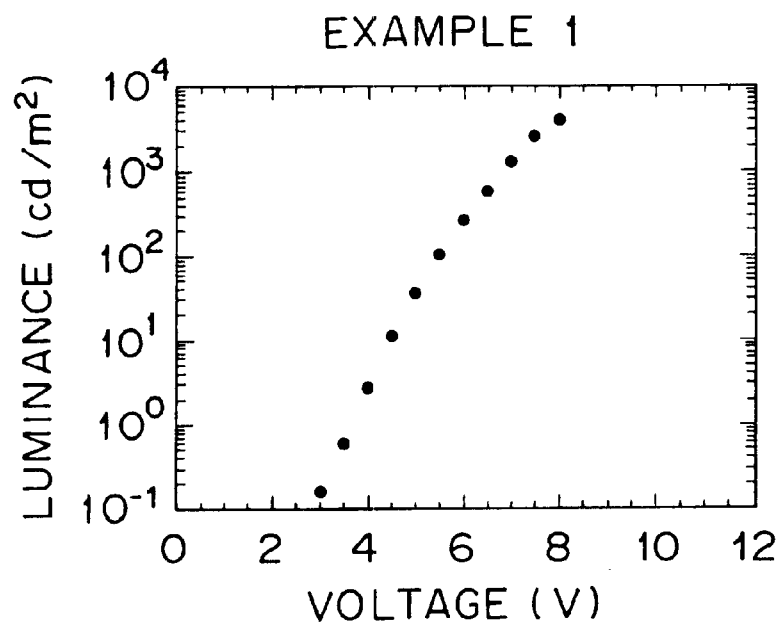
FIG. 10 is a graph showing a voltage-luminance characteristic of an organic electroluminescent device of Example 1 of the invention.

Luminescent characteristics of the device were evaluated by applying a forward bias DC voltage to the thus fabricated organic electroluminescent device of Example 1 in an atmosphere of nitrogen. The luminescent color was red, and the device was then subjected to spectral measurement, with the result that, as shown in FIG. 6, spectra having a luminescent peak at 660 nm were obtained. The spectral measurement was performed by use of a spectroscope made by Otsuka Electronic Co., Ltd. and using a photodiode array as a detector. Moreover, when the device was subjected to voltage-luminance measurement, there could be obtained a luminance of 4000 cd/m² at 8 V as particularly shown in FIG. 10.

Chemical formula 5

Structural formula (4)-1:

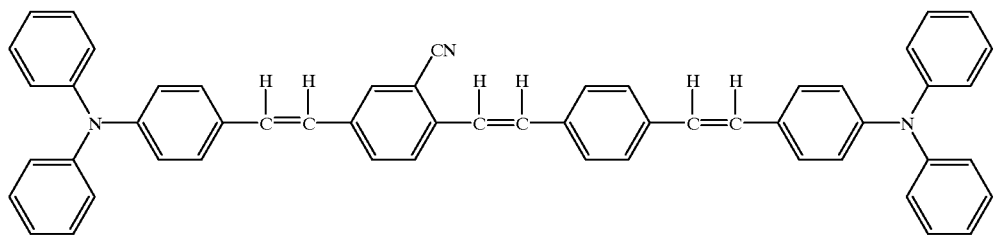

After the fabrication of the organic electroluminescent device, the device was allowed to stand over one month in an atmosphere of nitrogen, no device degradation was observed. In addition, when the device was subjected to forced degradation wherein continuous light emission was carried out at an initial luminance of 300 cd/m$^2$ while keeping a current at a given level. As a consequence, it took 2200 hours before the luminance was reduced to half.

EXAMPLE 2

This example illustrates fabrication of an organic electroluminescent device having a single hetero structure using, as an electron transport luminescent material, a compound of the structural formula (4)-1 selected among the distyryl compounds of the general formula (1), wherein $R^1$, $R^2$, $R^3$ and $R^4$, respectively, represent a phenyl group and $R^6$ represents a cyano group.

A 30 mm×30 mm glass substrate, which had been formed with a 100 nm thick anode made of ITO on one surface thereof, was set in a vacuum deposition apparatus. A metallic mask having a plurality of 2.0 mm×2.0 mm unit openings was placed, as a deposition mask, closely to the substrate. α-NPD (α-naphthylphenyldiamine) of the following structural formula was subjected to vacuum deposition at a vacuum of $10^{-4}$ Pa or below to form, for example, a 50 nm thick hole transport layer. The deposition rate was at 0.1 nm/second.

Chemical formula 7 a-NPD:

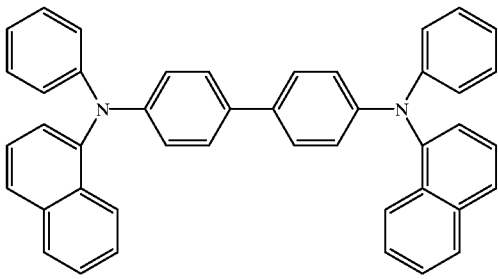

Further, the compound of the structural formula (4)-1 used as an electron transport material was vacuum deposited in contact with the hole transport layer. The thickness of the electron transport layer (serving also as a luminescent layer) composed of the compound of the structural formula (4)-1 was set, for example, at 50 nm, and the deposition rate was at 0.2 nm/second.

A built-up film of Mg and Ag provided as a cathode material was used. More particularly, Mg and Ag were, respectively, deposited at a deposition rate of 1 nm/second to form, for example, a 50 nm thick Mg film and a 150 nm thick Ag film. In this way, an organic electroluminescent device of Example 2 as shown in FIG. 3 was fabricated.

Figure 7:
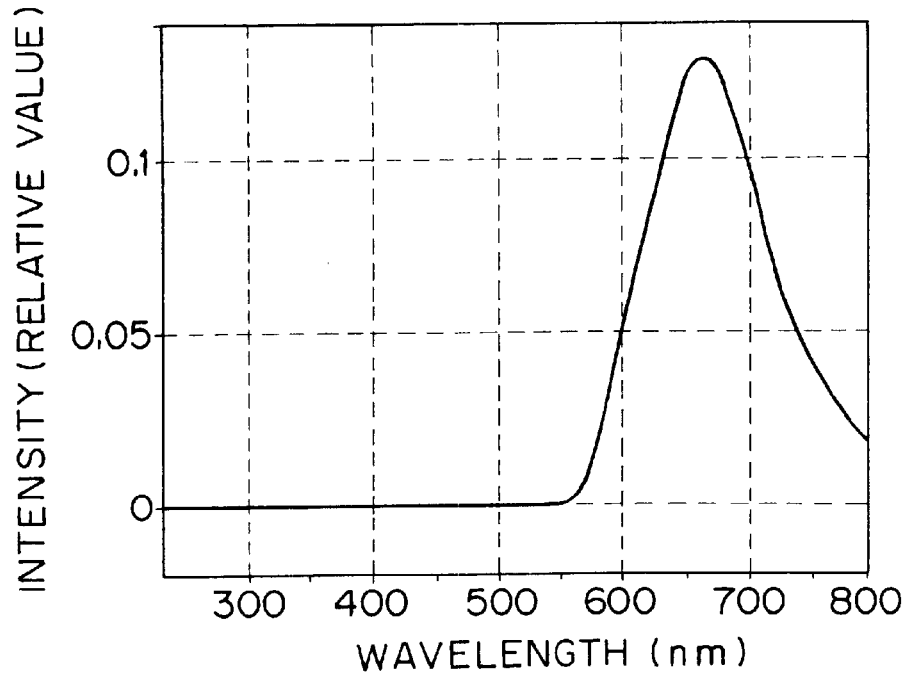
FIG. 7 is an emission spectrogram of an organic electroluminescent device of Example 2 of the invention.
Figure 8:
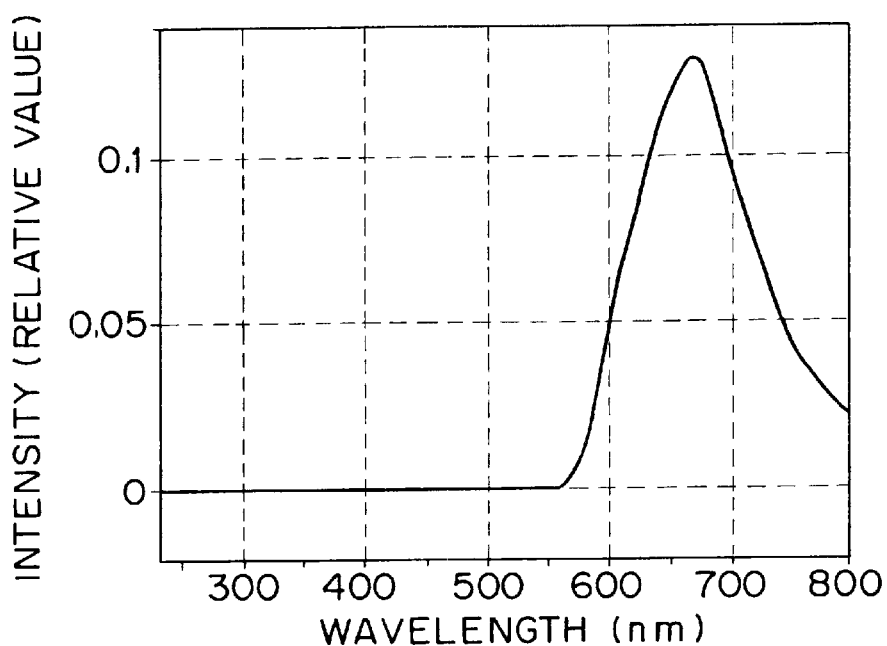
FIG. 8 is an emission spectrogram of an organic electroluminescent device of Example 3 of the invention.
Figure 11:
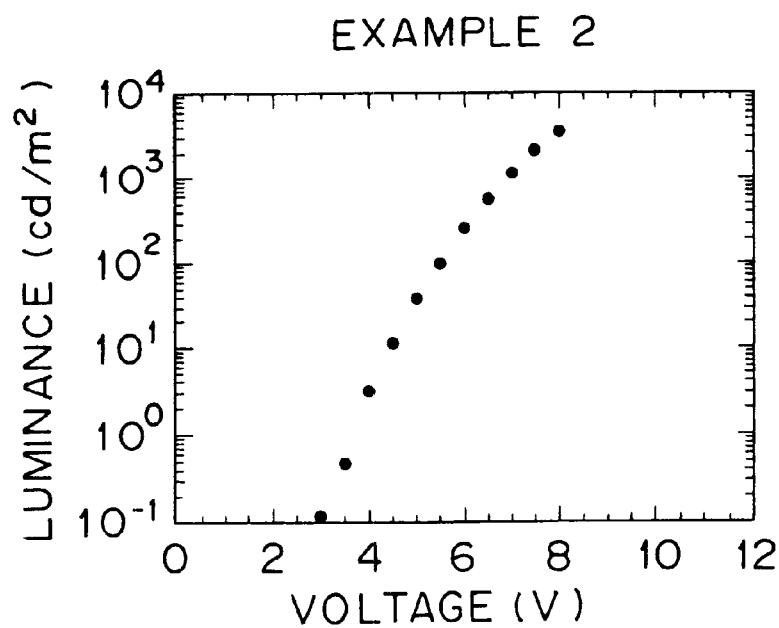
FIG. 11 is a graph showing a voltage-luminance characteristic of an organic electroluminescent device of Example 2 of the invention.

Luminescent characteristics were evaluated by applying a forward bias DC voltage to the thus fabricated organic electroluminescent device of Example 2 in an atmosphere of nitrogen. The luminescent color was red, and the device was then subjected to spectral measurement as in Example 1, with the result that, as shown in FIG. 7, spectra having a luminescent peak at 660 nm were obtained. Moreover, when the device was subjected to voltage-luminance measurement, there could be obtained a luminance of 3600 cd/m$^2$ at 8 V as is particularly shown in FIG. 11.

After the fabrication of the organic electroluminescent device, the device was allowed to stand over one month in an atmosphere of nitrogen, no degradation of the device was observed. In addition, when the device was subjected to forced degradation wherein continuous light emission was carried out at an initial luminance of 300 cd/m$^2$ while keeping a current at a given level. As a consequence, it took 2000 hours before the luminance was reduced to half.

EXAMPLE 3

This example illustrates fabrication of an organic electroluminescent device having a double hetero structure using, as a luminescent material, a compound of the structural formula (4)-1, selected among distyryl compounds of the general formula (1), wherein $R^1$, $R^2$, $R^3$ and $R^4$, respectively, represent a phenyl group and $R^6$ represents a cyano group.

A 30 mm×30 mm glass substrate, which had been formed with a 100 nm thick anode made of ITO on one surface thereof, was set in a vacuum deposition apparatus. A metallic mask having a plurality of 2.0 mm×2.0 mm unit openings was placed, as a deposition mask, near the substrate, followed by subjecting α-NPD (α-naphthylphenyldiamine) of the afore-indicated structural formula to vacuum deposition at a vacuum of $10^{-4}$ Pa or below to form, for example, a 30 nm thick hole transport layer. The deposition rate was at 0.2 nm/second.

Further, the compound of the afore-indicated structural formula (4)-1 used as a luminescent material was vacuum deposited in contact with the hole transport layer. The thickness of the luminescent layer composed of the compound of the structural formula (4)-1 was set, for example, at 30 nm, and the deposition rate was at 0.2 nm/second.

Alq$_3$ of the afore-indicated structural formula used as an electron transport material was deposited in contact with the luminescent layer. The thickness of the Alq$_3$ layer was set, for example, at 30 nm, and the deposition rate was at 0.2 nm/second.

A built-up film of Mg and Ag provided as a cathode material was used. More particularly, Mg and Ag were, respectively, deposited at a deposition rate of 1 nm/second to form, for example, a 50 nm thick Mg film and a 150 nm thick Ag film. In this way, an organic electroluminescent device of Example 3 as shown in FIG. 4 was fabricated.

Figure 12:
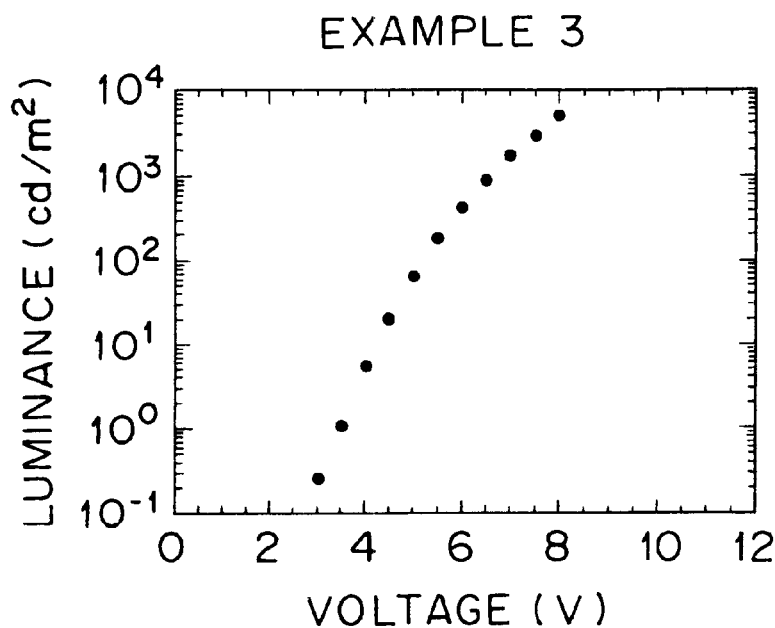
FIG. 12 is a graph showing a voltage-luminance characteristic of an organic electroluminescent device of Example 3 of the invention.

Luminescent characteristics of the device were evaluated by applying a forward bias DC voltage to the thus fabricated organic electroluminescent device of Example 3 in an atmosphere of nitrogen. The luminescent color was red, and the device was subjected to spectral measurement, with the result that spectra having a luminescent peak at 660 nm were obtained. Moreover, when the device was subjected to voltage-luminance measurement, there could be obtained a luminance of 4800 cd/m$^2$ at 8 V as shown in FIG. 12.

After the fabrication of the organic electroluminescent device, the device was allowed to stand over one month in an atmosphere of nitrogen, no degradation of the device was observed. In addition, when the device was subjected to forced degradation wherein continuous light emission was carried out at an initial luminance of 300 cd/m$^2$ while passing a current at a given level. As a consequence, it took 3800 hours before the luminance was reduced to half.

EXAMPLE 4

The general procedure of Example 2 was repeated with respect to the layer arrangement and the film formation procedures except that TPD (triphenyldiamine derivative) of the following structural formula was used as a hole transport material in place of α-NPD, thereby fabricating an organic electroluminescent device.

Chemical formula 8

TPD:

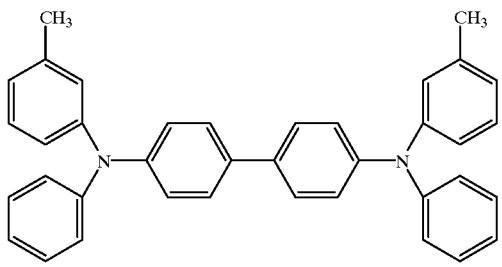

The organic electroluminescent device of this example assumed red luminescence, like Example 2. The results of spectral measurement reveal that spectra were in coincidence with those of the organic electroluminescent device of Example 2.

EXAMPLE 5

This example illustrates the fabrication of an organic electroluminescent device having a single hetero structure using, as a hole transporting luminescent material, a compound of the following structural formula (4)-2 selected among the distyryl compounds of the general formula (1), wherein $R^1$ and $R^4$, respectively, represent a phenyl group, $R^2$ and $R^3$, respectively, represent a 4-methoxyphenyl group and $R^6$ represents a cyano group structural formula (4)-2.

Chemical formula 9 structural formula (4)-2:

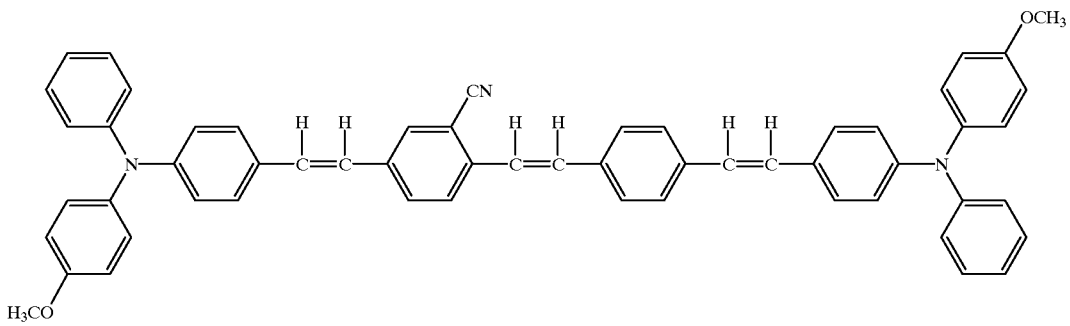

A 30 mm×30 mm glass substrate, which had been formed with a 100 nm thick anode made of ITO on one surface thereof, was set in a vacuum deposition apparatus. A metallic mask having a plurality of 2.0 mm×2.0 mm unit openings was placed, as a deposition mask, near the substrate, followed by subjecting the compound of the afore-indicated structural formula (4)-2 to vacuum deposition at a vacuum of $10^{-4}$ Pa or below to form, for example, a 50 nm thick hole transport layer (serving also as a luminescent layer). The deposition rate was at 0.1 nm/second.

Further, $Alq_3$ (tris(8-quinolinol)aluminium) of the afore-indicated structural formula used as an electron transport layer was vacuum deposited in contact with the hole transport layer. The thickness of the electron transport layer composed of $Alq_3$ was set, for example, at 50 nm, and the deposition rate was at 0.2 nm/second.

A built-up film of Mg and Ag provided as a cathode material was used. More particularly, Mg and Ag were, respectively, deposited at a deposition rate of 1 nm/second to form, for example, a 50 nm thick Mg film and a 150 nm thick Ag film. In this way, an organic electroluminescent device of Example 5 as shown in FIG. 3 was fabricated.

Figure 9:
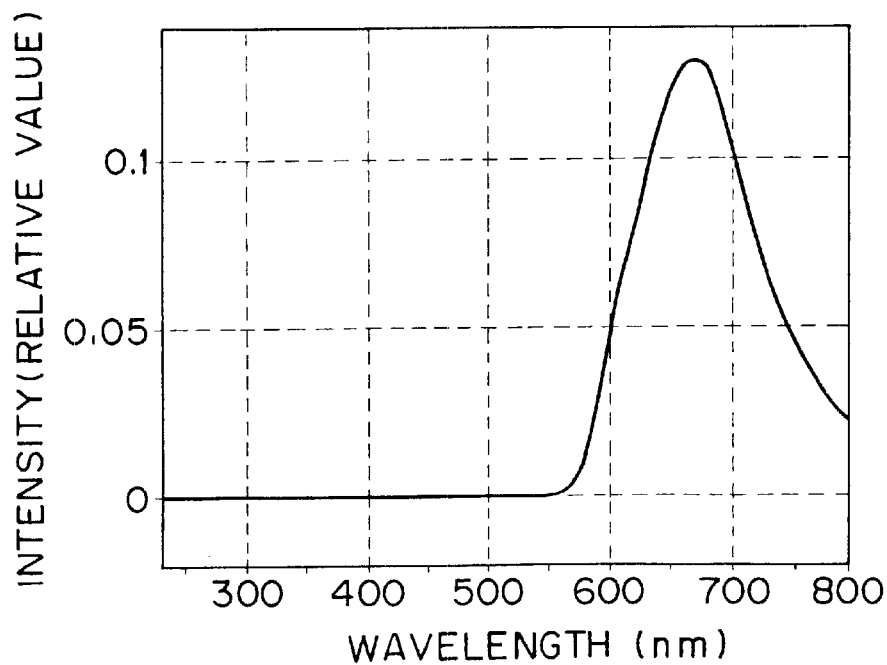
FIG. 9 is an emission spectrogram of an organic electroluminescent device of Example 5 of the invention.
Figure 13:
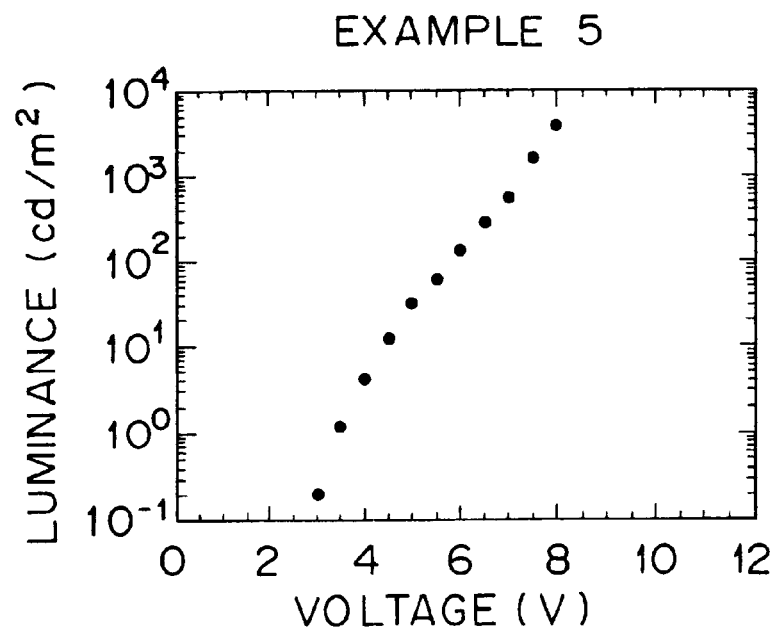
FIG. 13 is a graph showing a voltage-luminance characteristic of an organic electroluminescent device of Example 5 of the invention.

Luminescent characteristics of the device were evaluated by applying a forward bias DC voltage to the thus fabricated organic electroluminescent device of Example 5 in an atmosphere of nitrogen. The luminescent color was red, and the device was subjected to spectral measurement, as shown in FIG. 9 with the result that spectra having a luminescent peak at 670 nm were obtained. The spectral measurement was performed by use of a spectroscope made by Otsuka Electronic Co., Ltd. and using a photodiode array as a detector. Moreover, when the device was subjected to voltage. Moreover, when the device was subjected to voltage-luminance measurement, there could be obtained a luminance of 3400 $cd/m^2$ at 8 V as shown in FIG. 13.

After the fabrication of the organic electroluminescent device, the device was allowed to stand over one month in an atmosphere of nitrogen, no degradation of the device was observed. In addition, when the device was subjected to forced degradation wherein continuous light emission was carried out at an initial luminance of 300 $cd/m^2$ while passing a current at a given level. As a consequence, it took 1800 hours before the luminance was reduced to half.

As will be apparent from the foregoing, when the organic layer provided between an anode and a cathode in an electroluminescence device contains at least one distyryl compound of the general formula (1) or (3), the organic electroluminescent device has high luminance and ensures stable red color luminescence.

What is claimed is:

1. An organic electroluminescent device of the type which comprises an organic layer which has a luminescent region and is provided between an anode and a cathode and which contains, as an essential component, an organic material capable of generating luminescence by application, of an electric current, wherein said organic layer contains, as an organic luminescent material, a distyryl compound represented by the following general formula (1) or (3)

Chemical formula 1 general formula (1):

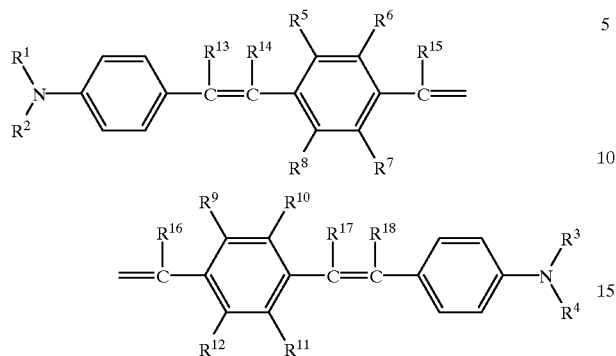

wherein $R^1$, $R^2$, $R^3$ and $R^4$ are, respectively, groups which may be the same or different and independently represent an aryl group of the following general formula (2), Chemical formula general formula (2):

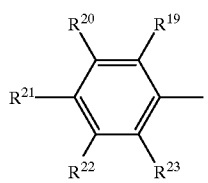

wherein $R^{19}$, $R^{20}$, $R^{21}$, $R^{22}$ and $R^{23}$ are, respectively, groups which may be the same or different and may represent a hydrogen atom, provided that at least one of them represents a saturated or unsaturated alkoxyl group, an alkyl group, an amino group or an alkylamino group, and $R^5$, $R^6$, $R^7$, $R^8$, $R^9$, $R^{10}$, $R^{11}$, $R^{12}$, $R^{13}$, $R^{14}$, $R^{15}$, $R^{16}$, $R_{17}$ and $R^{18}$ are groups which may be the same or different, provided that at least one of them represents a cyano group, a nitro group or a halogen atom.

general formula (3):

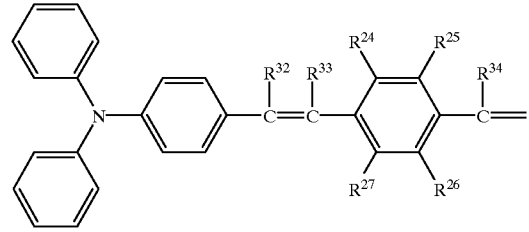

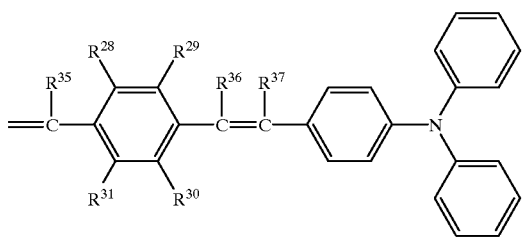

wherein $R^{24}$ $R^{25}$ $R^{26}$ $R^{27}$ $R^{28}$ $R^{29}$ $R^{30}$ $R^{31}$ $R^{32}$ $R^{33}$ $R^{34}$ $R^{35}$, $R^{36}$ and $R^{37}$ are groups which may be the same or different (and represent a hydrogen atom) provided that at least one of them represents a cyano group, a nitro group or a halogen atom I.

2. An organic electroluminescent device according to claim 1, wherein said organic layer has an organic successively built-up structure wherein a hole transport layer and an electron transport layer are built up, and said distyryl compound is used as a material for forming said hole transport layer.

3. An organic electroluminescent device according to claim 1, wherein said organic layer has an organic built-up structure wherein a hole transport layer and an electron transport layer are successively built up, and said distyryl compound is used as a material for forming said electron transport layer.

4. An organic electroluminescent device according to claim 1, wherein said organic layer has an organic built-up structure wherein a hole transport layer, a luminescent layer, and an electron transport layer are built up, and said distyryl compound is used as a material for forming said luminescent layer.

5. An organic electroluminescent device of the type which comprises an organic layer having a luminescent region and provided between an anode and a cathode, wherein said organic layer comprises, as an organic luminescent material, at least one of distyryl compounds represented by the following structural formulae (4)-1, (4)-2, (4)-3, (4)-4, (4)-5, (4)-6 and (4)-7

Chemical formula 2
general formula (4)-1:
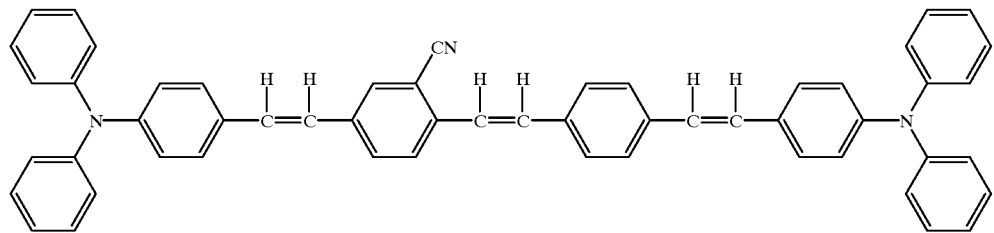
general formula (4)-2:
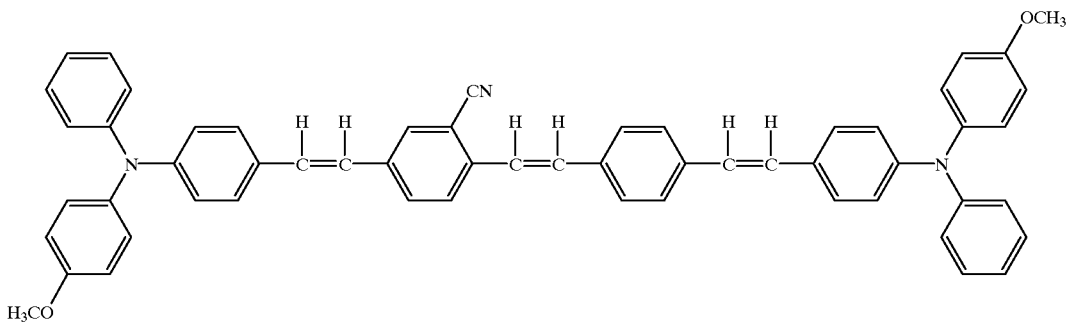
general formula (4)-3:
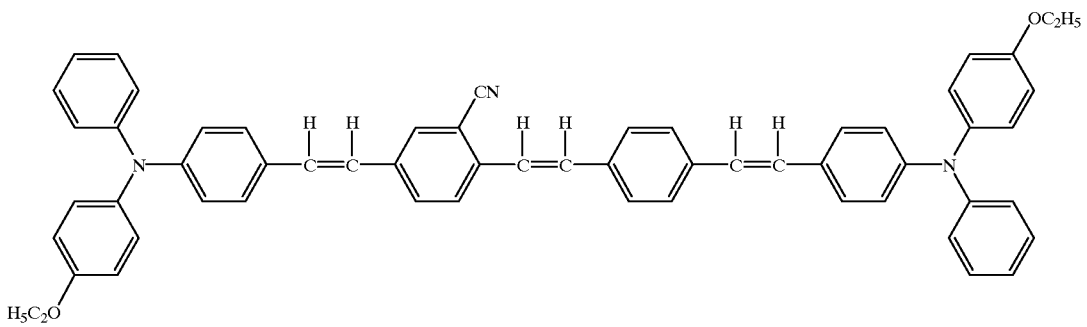
general formula (4)-4:
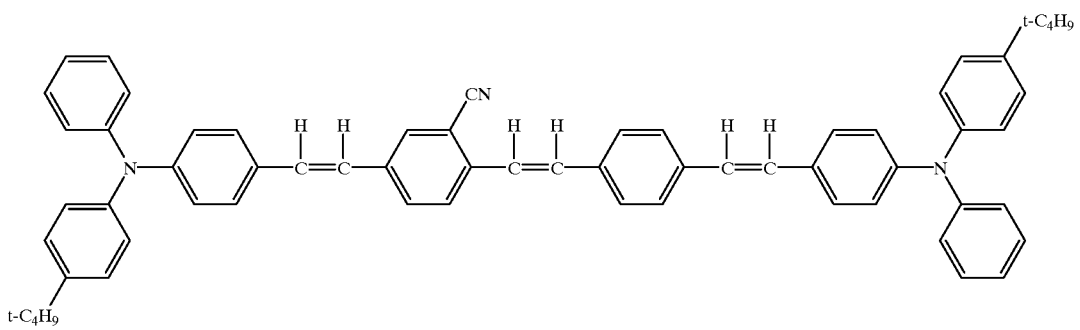

general formula (4)-5:

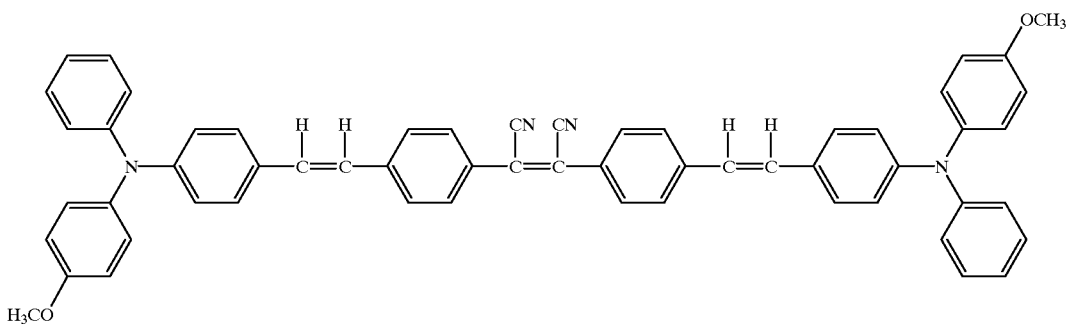

general formula (4)-6:

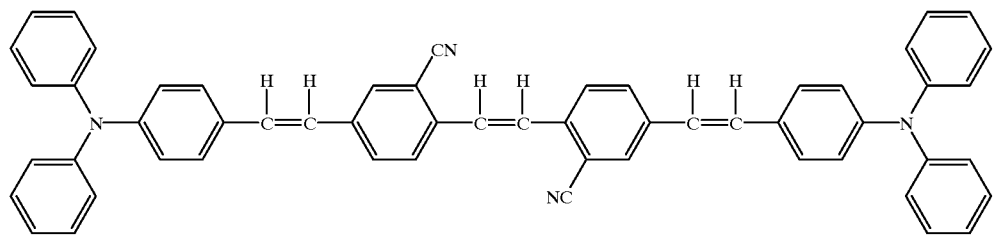

general formula (4)-7:

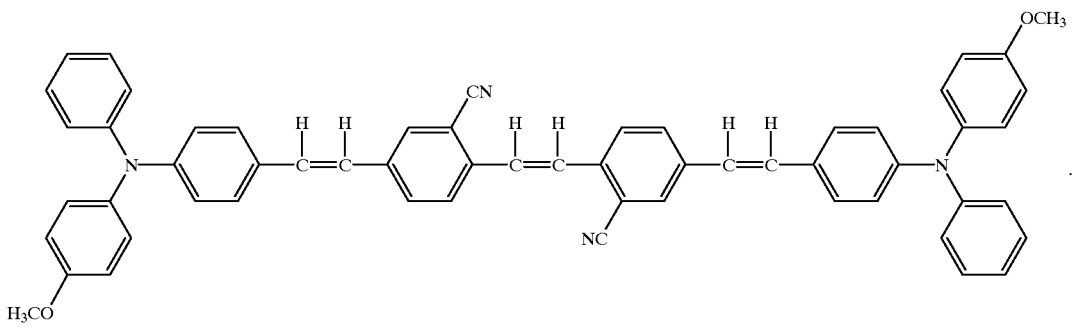

6. An organic electroluminescent device according to claim 5, wherein said organic layer has an organic built-up structure wherein a hole transport layer and an electron transport layer are built up, and said distyryl compound is used as a material for forming said hole transport layer.

7. An organic electroluminescent device according to claim 5, wherein said organic layer has an organic built-up structure wherein a hole transport layer and an electron transport layer are successively built up, and said distyryl compound is used as a material for forming said electron transport layer.

8. An organic electroluminescent device according to claim 5, wherein said organic layer has an organic built-up structure wherein a hole transport layer, a luminescent layer, and an electron transport layer are built up, and said distyryl compound is used as a material for forming said luminescent layer.

* * * * *